US007718831B2

(12) United States Patent
Chan et al.

(10) Patent No.: US 7,718,831 B2
(45) Date of Patent: May 18, 2010

(54) METHOD FOR ASYMMETRIC HYDROSILYLATION OF KETONES

(75) Inventors: Albert S Chan, Hung Hom (HK); Jianxin Ji, Nashville, TN (US); Jing Wu, Hangzhou (CN)

(73) Assignee: The Hong Kong Polytechnic University, Kowloon Hong Kong (HK)

( * ) Notice: Subject to any disclaimer, the term of this patent is extended or adjusted under 35 U.S.C. 154(b) by 325 days.

(21) Appl. No.: 11/816,139

(22) PCT Filed: Feb. 16, 2006

(86) PCT No.: PCT/US2006/005669

§ 371 (c)(1),
(2), (4) Date: Aug. 13, 2007

(87) PCT Pub. No.: WO2006/089129

PCT Pub. Date: Aug. 24, 2006

(65) Prior Publication Data

US 2008/0269490 A1 Oct. 30, 2008

Related U.S. Application Data

(60) Provisional application No. 60/654,581, filed on Feb. 18, 2005.

(51) Int. Cl.
C07C 29/143 (2006.01)
B01J 31/24 (2006.01)
B01J 31/18 (2006.01)
(52) U.S. Cl. ........................ 568/814; 568/809; 568/880; 568/881
(58) Field of Classification Search ........................ None
See application file for complete search history.

(56) References Cited

U.S. PATENT DOCUMENTS 5,886,182 A 3/1999 Chan et al. ..................... 546/21
6,680,385 B2 1/2004 Chan et al. .................. 544/329

OTHER PUBLICATIONS

Pai et al., 122 J. Am. Chem. Soc., 11513-514 (2000).*
Sirol et al., Organic Letters, vol. 3, No. 25, pp. 4111-4113, "Efficient enantioselective hydrosilylation of ketones catalyzed by air stable copper fluoride-phosphine complexes" (2001).
Wang et al., Journal of Molecular Catalysis A: Chemical, vol. 196, No. 1, pp. 171-178, "Enantioselective bis-alkoxycarbonylation of styrene catalyzed by novel chiral dipyridylphosphine cationic palladium(II) complexes" (2003).
Wu et al., Proceedings of the National Academy of Sciences of the United States of America, vol. 102, No. 10, pp. 3570-3575, "A remarkably effective copper(II)-dipyridylphosph8ine catalyst system for the asymmetric hydrosilylation of ketones in air" 2005).
Wu et al.,.Tetrahedron: Asymmetry, vol. 14, issue 8, pp. 987-992, "Studies on the rhodium- and ruthenium-catalyzed asymmetric hydrogenation of α-dehydroamino acids using a family of chiral dipyridylphosphine ligand (P-Phos)" (2003).
Wu et al., Tetrhedron Letters, vol. 43, issue 8, pp. 1539-1543, "A new chiral dipyridylphosphine ligand Xyl-P-Phos and its application in the Ru-catalyzed asymmetric hydrogenation of β-ketoesters" (2002).
Xu et al., Chem. Communication, vol. 11, pp. 1390-1392, "Air-stable Ir-(P-Phos) complex for highly enantioselective hydrogenation of quinolines and their immobilization in poly(ethylene glycol) dimethyl ether (DMPEG)" (2005).
Brown et al., "Determination of the enantiomeric excesses of chiral acids by 19F NMR studies of their esters deriving from (R)-(+)-2-(Trifluoromethyl)benzhydrol", Tetrahedron Asymmetry, vol. 5, No. 7, pp. 1191-1194 (1994).
Brunner et al., "Asymmetric catalysis" Jornal of Organometallic Chemistry, 346, pp. 413-424 (1988)r.
Brunner et al., "Asymmetrische Katallysen" Journal of Organometallic Chemistry, 275, C17-C21 (1984).
Burk et al., "A catalyst for efficient and highly enantioselective hydrogenation of aromatic, heteroaromatic and alpha,beta-unsaturated ketones", Organic Letters, vol. 2, No. 26, pp. 4173-4176 (2000).
Cao et al., "Ru-BICP-catalyzed asymmetric hydrogenation of aromatic ketones", J. Org. Chem., 64, pp. 2127-2129 (1999).
Carter et al, "Enantioselective hydrosilylation of ketones with a chiral titanocene catalyst", J. Am. Chem. Soc., 116, pp. 11667-11670 (1994).
Chaplin et al., "Industrially viable syntheses of highly enantiomerically enriched 1-aryl alcohols via asymmetric hydrogenation", Organic Process Research & Development 7, pp. 89-94 (2003).

(Continued)

*Primary Examiner*—Brian J Davis
(74) *Attorney, Agent, or Firm*—Sandra S. Shim; John W. Kung

(57) ABSTRACT

Method of asymmetrically hydrosilylating substrates using catalysts having a ligand of the compound of the formula (I)

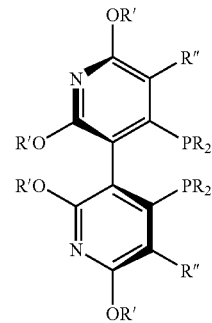

Compound (1)

wherein
R is optionally substituted alkyl, cycloalkyl, aryl or heteroaryl;
R' is hydrogen, optionally substituted lower alkyl; and
R'' is hydrogen, halogen, optionally substituted alkyl, hydroxy, amino (e.g., primary, secondary or tertiary), alkenyl;
or an enantiomer thereof; or an enantiomeric mixture thereof with a transition metal. Particularly suitable reactions include the asymmetric hydrosilylation of ketones.

19 Claims, No Drawings

OTHER PUBLICATIONS

Corriu et al., "Selective catalytic route to bifunctional silanes. Catalysis by rhodium and ruthenium complexes of the alcoholysis of diarylsilanes and the hydrosilylation of carbonyl compounds" J.C.S. Chem. Comm., pp. 38-39 (1973).

Dumont et al., "Asymmetric catalytic reduction with transition metal complexes. II. Asymmetric catalysis by a supported chiral rhodium complex[1]", J. Am. Chem. Soc. 95:25, pp. 8295-8299, (1973).

Gade et al., "A modular assembly of chiral oxazolinylcarbene-rhodium complexes: efficient phosphane-free catalysts for the asymmetric hydrosilylation of dialkyl ketones", Angew. Chem., Int. Ed. 43, pp. 1014-1016 (2004).

Genov et al., "Asymmetric hydrogenation of ketones catalyzed by $Ru^{II}$-bisp complexes", Angew. Chem. Int. Ed., 43, pp. 2816-2819 (2004).

Henschke et al., "A conscise synthesis of a nes xylyl-biaryl diphosphine ligand for asymmetric hydrogenation of ketones", Tetrahedron Letters, vol. 44, issue 23, pp. 4379-4383 (2003).

Imma et al., "Asymmetric catalytic hydrosilylation of ketones with triethoxysilane using a chiral binaphthol -titanium complex" SYNLETT, pp. 1229-1230 (1996).

Lawrence et al., "An efficient protocol for the reduction of ketones with tin(II) complexes and PMHS ", Tetrahedron Letters, vol. 41, issue 22, pp. 4507-4512 (2000).

Lawrence et al., "Polymethylhydrosiloxane: a versatile reducing agent for organic synthesis", J. Chem. Soc., Perkin Trans. I, pp. 3381-3391 (1999).

Lipshutz et al., "Asymmetric hydrosilylation of aryl ketones catalyzed by copper hydride complexed by nonracemic biphenyl bis-phosphine ligands", J. Am. Chem. Soc., 125, pp. 8779-8789 (2003).

Lipshutz et al., "Copper(I) hydride-catalyzed asymmetric hydrosilylation of heteroaromatic ketones", Organic Letters, vol. 4, No. 23, pp. 4045-4048 (2002).

Lipshutz et al., Ligand-accelerated, copper-catalyzed asymmetric hydrosilylations of aryl ketones, J. Am. Chem. Soc., vol. 123, No. 51, pp. 12917-12918 (2001).

Mimoun et al., "Enantioselective reduction of ketones by polymethylhydrosiloxane in the presence of chiral zinc catalysts", J. Am. chem. soc., 121, pp. 6158-6166 (1999).

Naito et al., "Enantioresolution of fluorinated diphenylmethanols and determination of their absolute configurations by X-ray crystallographic and $^1H$ NMR anisotropy methods", Chirality 16: pp. 22-35 (2004).

Nishibayashi et al., "Ruthenium-catalyzed asymmetric-hydrosilylation of ketones and imine", Organometallics, 17, pp. 3420-3422 (1998).

Nishlyama et al., "Chiral and $C_2$-Symmetrical bis(oxazolinylpyridine)rhodium(III) complexes: effective catalysts for asymmetric hydrosilylation of ketones", Oranometallics, 8, pp. 846-848 (1989).

Noyori et al., "Asymmetric catalysis by architectural and functional molecular engineering: practical chemo- and stereoselective hydrogenation of ketones", Angew. Chem. Int. Ed. 40, pp. 40-73 (2001).

Noyori, Asymmetric catalysis: science and opportunities (Nobel Lecture), Angew. Chem. Int. Ed. 41, pp. 2008-2022 (2002).

Ohkuma et al., "Asymmetric hydrogenation of alkenyl, cyclopropyl, and aryl ketones, $RuCl_2$(xylbinap)(1,2-diamine) as a precatalyst exhibiting a wide scope", J. Am. Chem. Soc. 120, pp. 13529-13530 (1998).

Ohkumo et al., "Selective hydrogenation of benzophenones to benzhydrols. Asymmetric synthesis of unsymmetrical diarylmethanols", Organic Letters, vol. 2, No. 5, pp. 659-662 (2000).

Ojima et al., "Reduction of carbonyl compounds with various hydrosilane-rhodium(I) complex combinations", BCSJAB vol. 45, No. 11, p. 3506 (1972).

Ojima et al., "Rhodium complex catalysed hydrosilylation of carbonyl compounds", Journal of the Chemical Society, 16, p. 938 (1972).

Ojima et al., "Stereoselective reduction of ketones with hydrosilane-rhodium(I) complex combinations", BCSJA8, vol. 45, No. 12, p. 3722 (1972).

Pai et al., "Highly effective chiral dipyridylphosphine ligands: synthesis, structural determination, and applications in the Ru-catalyzed asymmetric hydrogenation reactions", J. Am. Chem. Soc. 122, pp. 11513-11514 (2000).

Rahimian et al., "The influence of the catalyst preparation protocol and silane structure on the rate and enantioselectivity of ansa-titanocene catalysed hydrosilation of prochiral ketones [1]", Inorganica Chimica Acta 270, pp. 330-336 (1998).

Rekker et al., " The antihistaminic and anticholinergic activities of optically active diphenhydramine derivatives" Arzneim. Forsch. (Drug Res.), Jahrgang 21, Nr. 5 , pp. 688-691 (1971).

Saito et al., "New chiral diphosphine ligands designed to have a narrow dihedral angle in the biaryl backbone" , Adv. Synth. Catal., 343, No. 3. pp. 264-267 (2001).

Sawamura et al., "*trans*-chelating chiral diphosphane ligands bearing flexible *P*-alkyl substituents (alkylTRAPs) and their application to the rhodium-catalyzed asymmetric hydrosilylation of simple ketones" Angew. Chem. Int. Ed. 33, No. 1, pp. 111-113 (1994).

Scalone et al., "Efficient enantioselective synthesis of the NMDA 2b receptor antagonist Ro 67-8867", Organic Process Research & Development 7, pp. 418-425 (2003).

Schmid et al., "New developments in enantioselective hydrogenation", Pure & Appl. Chem., vol. 68. No. 1, pp. 131-138 (1996).

Schmid et al., "Axially dissymmetric diphosphines in the biphenyl series: synthesis of (6,6'dimethoxybiphenyl-2,2'-diyl)bis(diphenylphosphine) ('MeO-BIPHEP') and analogues via an ortho-lithiation/iodination Ullmann-reaction approach", Helvetica Chimica Acta, 74, pp. 370-389 (1991).

Sudo et al., "An efficient phosphorous-containing oxazoline ligand derived from *cis*-2-amino-3,3-dimethyl-1-indanol: application to the rhodium-catalyzed enantioselective hydrosilylation of ketones", Tetrahedron: Asymmetry, vol. 8, issue 19, pp. 3205-3208 (1997).

Tao et al., Application of a new family of P,N. ligands to the highly enantioselective hydrosilylation of aryl alkyl and dialkyl ketones**, Angew. Chem. Int. Ed. 41, No. 20, pp. 3892-3894 (2002).

van der Stelt et al., "The resolution in optical isomers of orphenadrine, 4-methyldiphenhydramine and their *n*demethyl derivatives", Arzneim. Forsch. 19, Heft 12, pp. 2020-2012 (1969).

Wu et al., "Air-stable catalysts for highly efficient and enantioselective hydrogenation of aromatic ketones", J. Org. Chem, 67, pp. 7908-7910 (2002).

Wu et al., "Chiral [$RuCl_2$(dipyridylphosphane)(1,2-diamine)] catalysts: applications in asymmetric hydrogenation of a wide range of simple ketones", Chem. Eur. J. 9, pp. 2963-2968 (2003).

Wu et al., "Ru-catalyzed highly enantioselective hydrogenation of β-alkyl-substituted β-(acylamino)acrylates", J. Org. Chem, 68, pp. 2490-2493 (2003).

Wu et al., Synthesis and structural characterization of a highly effective chiral dipyridylphosphine ligand and its application in the Ru-catalyzed asymmetric hydrogenation of β-ketoesters, Synlett, SI, pp. 1050-1054 (2001).

Wu et al. "A remarkably effective copper (II)-dipyridylphosphine catalyst system for the asymmetric hydrosilylation of ketones in air", PNAS, vol. 102, No. 10, pp. 3570-3575 (2005).

Xie et al., "Synthesis of spiro diphosphines and their application in asymmetric hydrogenation of ketones", J. Am. Chem. Soc., 125, pp. 4404-4405 (2003).

Yun et al., "Titanocene-catalyzed asymmetric ketone hydrosilylation: the effect of catalyst activation protocol and additives on the reaction rate and enantioselectivity", J. Am. Chem. Soc., 121, 5640-5644 (1999).

Zhu et al., "Asymmetric hydrosilylation of ketones catalyzed by ruthenium complexes with chiral tridentate ligands", Journal of Organometallic Chemistry 547, pp. 97-101 (1997).

* cited by examiner

METHOD FOR ASYMMETRIC HYDROSILYLATION OF KETONES

This application claims benefit of Provisional Application No. 60/654,581, filed Feb. 18, 2005.

FIELD OF THE INVENTION

The present invention relates to a method of using asymmetric hydrosilylation to convert ketones into alcohols, e.g., secondary alcohols.

BACKGROUND OF THE INVENTION

Considerable effort has been devoted to the development of efficient methods for the preparation of enantiomerically pure secondary alcohols due to the significance of these intermediates, e.g., in the manufacture of pharmaceuticals. The catalytic asymmetric reduction of prochiral ketones as a direct route to enantiomeric alcohols is among the most studied and developed strategies. Although intensive studies have focused on the asymmetric hydrogenation which shows excellent enantioselectivities for a wide range of simple ketones, asymmetric hydrosilylation has also attracted much attention because of the mild reaction conditions used and its technical simplicity.

The asymmetric hydrosilylations of prochiral simple ketones mediated by catalysts of rhodium(I) and ruthenium (II), titanium, zinc, tin and copper(I) have been extensively explored. Unfortunately, many of these reactions are routinely conducted at a low substrate-to-ligand ratio (S/L), from 50 to 500. The high cost of catalyst and the low substrate-to-catalyst ratio renders the previous hydrosilylation work commercially unattractive.

More recently, Lipshutz et al, developed a catalyst system formed in situ from CuCl and nonracemic bidentate phosphines (e.g., 3,5-xyl-MeO-BIPHEP or DTBM-SEGPHOS) along with t-BuONa. See Lipshutz et al, *Ligand-accelerated, copper-catalyzed asymmetric hydrosilylations of aryl ketones;* 123 J. AM. CHEM. SOC. 12917-18 (2001). This system allowed for highly active and enantioselective hydrosilylations of both aryl alkyl and heteroaromatic ketones in the presence of an inexpensive stoichiometric reductant, polymethylhydrosiloxane (PMHS), even at a S/L up to 100,000 which approached the levels achieved in related ruthenium-based asymmetric hydrogenations. The reactions, however, must be performed using standard Schlenk techniques and at low temperatures (e.g., from −50° C. to −78° C.) for maximum enantiomeric excess (ee). Moreover, the presence of a base, such as t-BuONa, was critical for the generation of the active catalyst.

Olivier Riant et al. also recently reported a base-free and air-accelerated $CuF_2$/BINAP/$PhSiH_3$ system for the same transformation which furnished secondary alcohols in moderate to good enantioselectivites under ambient conditions at lower S/L ratios of 100-200. See Sabine Sirol et al., *Efficient enantioselective hydrosilylation of ketones catalyzed by air stable copper fluoride-phosphine complexes*, 3 ORG. LETT. 4111-13 (2001). Although Riant's system is air-stable and conducted at mild reaction temperatures, the activities, enantioselectivities and substrate scope are not comparable to those described by Lipshutz.

Thus, there is a need for a catalyst system for the process for preparing secondary alcohols that results in high reactivities and enantioselectivities and conducted under mild conditions, normal atmosphere and without the addition of a base. The present invention addresses this need.

SUMMARY OF THE INVENTION

The present invention relates to a method of converting a substrate, e.g., a ketone in the presence of a catalyst into an enantiomeric alcohol. More specifically, the methods of the present invention, utilize a transition metal catalyst having a transition metal bound to a compound of the following formula (I):

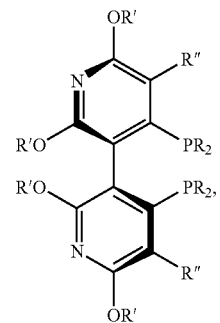

Compound (1)

wherein
R is optionally substituted alkyl, cycloalkyl, aryl or heteroaryl;
R' is hydrogen, optionally substituted lower alkyl; and
R" is hydrogen, halogen, optionally substituted alkyl, hydroxyl, amino (e.g., primary, secondary or tertiary), alkenyl;

or an enantiomer thereof; or an enantiomeric mixture thereof.

The methods of the present invention can be conducted in the presence of air, e.g., a normal atmosphere, and at mild temperatures, e.g., from room temperature to −20° C. Furthermore, the methods of the present invention do not require the use of an organic or inorganic base in the reaction. Additionally, the methods employ a S/L molar ratio, e.g., from 20,000-500,000, e.g., from 30,000-250,000, e.g., from 50,000-100,000.

In a particular embodiment, the transition metal catalyst is copper bound to the ligand (S)-2,2',6,6'-tetramethoxy-4,4'-bis-(diphenylphosphino)-3,3'-bipyridine or an enantiomer thereof and enantiomeric mixtures thereof. In another embodiment, the ligand is 2,2',6,6'-tetrametoxy-4,4'-bis[di(3,5-dimethylphenyl)phosphino]-3,3'-bipyridine or an enantiomer thereof and enantiomeric mixtures thereof.

In yet another particular embodiment, the reaction is the asymmetric hydrosilylation of a ketone to an alcohol. In a further embodiment, the reaction is the asymmetric hydrosilylation of a diaryl ketone to an alcohol.

DETAILED DESCRIPTION OF THE INVENTION

The present invention relates to a method of converting a prochiral substrate, e.g., a ketone, by an asymmetric reaction in the presence of a catalyst to an enantiomeric alcohol. More specifically, the present invention relates to the use of chiral dipyridylphospine ligands bound to a transition metal catalyst for the catalysis of reactions conducted under air atmosphere, or normal atmosphere, and at mild temperatures without the addition of an organic or inorganic base. Such chiral ligands are especially useful, e.g., for the air-accelerated, copper(II) catalyzed asymmetric hydrosilylations reactions.

Dipyridylphosphine ligands, as used herein, include compounds of the formula (I):

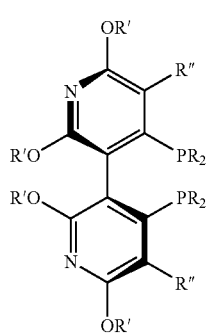

Compound (1)

wherein
R is optionally substituted alkyl, cycloalkyl, aryl or heteroaryl;
R' is hydrogen, optionally substituted lower alkyl; and
R" is hydrogen, halogen, optionally substituted alkyl, hydroxyl, amino (e.g., primary, secondary or tertiary), alkenyl;

or an enantiomer thereof; or an enantiomeric mixture thereof.

As used herein, the term "optionally substituted alkyl" refers to unsubstituted or substituted straight- or branched-chain hydrocarbon groups having one to twenty carbon atoms, e.g., one to seven carbon atoms. Examples of unsubstituted alkyl groups, include, but are not limited to, methyl, ethyl, propyl, isopropyl, n-butyl, t-butyl, isobutyl, pentyl, neopentyl, hexyl, isohexyl, heptyl, octyl and the like. Substituted alkyl groups include, but are not limited to, alkyl groups substituted by one or more of the following groups: hydroxyl, alkylamino, dialkylamino, cycloalkyl, alkenyl or alkoxy.

As used herein, the term "lower alkyl" refers to those optionally substituted alkyl groups as described above having one to six carbon atoms.

As used herein, the term "alkenyl" refers to any one of the above alkyl groups having at least two carbon atoms and further containing a carbon to carbon double bond at the point of attachment. Useful are groups having two to four carbon atoms.

As used herein, the terms "halogen", "halide" or "halo" refer to fluorine, chlorine, bromine and iodine.

As used herein, the term "alkoxy" refers to alkyl-O—.

As used herein, the term "cycloalkyl" refers to optionally substituted monocyclic aliphatic hydrocarbon groups of three to six carbon atoms, which may be substituted by one or more substitutents, such as alkyl or alkoxy.

Examples of monocylic hydrocarbon groups include, but are not limited to, cyclopropyl, cyclobutyl, cyclopentyl, cyclohexyl and the like.

As used herein, the term "aryl" refers to monocylic or bicyclic aromatic hydrocarbon groups having six to twelve carbon atoms in the ring portion, such as phenyl, biphenyl, naphthyl and tetrahydronaphthyl, each of which may optionally be substituted by one to four substituents, such as optionally substituted alkyl, cycloalkyl or alkoxy.

As used herein, the term "monocyclic aryl" refers to optionally substituted phenyl as described under aryl.

As used herein, the term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl or lower alkoxy.

Compounds of formula (I) and methods of their preparation are disclosed in U.S. Pat. No. 5,886,182 which is hereby incorporated by reference in its entirety.

When required, protecting groups may be introduced to protect the functional groups present from undesired reactions with reaction components under the conditions used for carrying out a particular chemical transformation of the present invention. The need and choice of protecting groups for a particular reaction is known to one skilled in the art and depends on the nature of the functional group to be protected (amino, hydroxy etc.), the structure and stability of the molecule of which the substituent is a part and the reaction conditions.

Well-known protecting groups that meet these conditions and their introduction and removal are described, e.g., in McOmie, *Protective Groups in Organic Chemistry*, Plenum Press, London, N.Y. (1973); and Greene and Wuts, *Protective Groups in Organic Synthesis*, John Wiley and Sons, Inc., NY (1999).

Particularly useful in the present invention are dipyridylphosphine compounds of formula (I), wherein R is optionally substituted aryl, R' is alkyl and R" is hydrogen or an enantiomer thereof; or an enantiomeric mixture thereof. Also particularly useful in the present invention are compounds of formula (I), wherein R is optionally substituted phenyl, R' is methyl, and R" is hydrogen. Exemplary embodiments of compound of formula (I) are: (S)-2,2',6,6'-tetramethoxy-4,4'-bis-(diphenylphosphino)-3,3'-bipyridine, also designated as (S)—P-Phos or (S)-1a; and 2,2',6,6'-tetrametoxy-4,4'-bis[di(3,5-dimethylphenyl)phosphino]-3,3'-bipyridine, also designated as (S)-Xyl-P-Phos or (S)-1b.

The dipyridylphosphine compounds of formula (I), as used in the present invention, e.g., have an optical purity of at least 85% ee, e.g., at least 95% ee, e.g., 98% ee.

The compounds of formula (I), as used in the present invention, can be converted to chiral transition metal catalysts by reacting a compound of formula (I) or an enantiomer thereof, or an enantiomeric mixture thereof, with a suitable transition metal salt, or a complex thereof, to generate a chiral transition metal catalyst that can be subsequently used in the present invention. The choice of a suitable transition metal salt, or a complex thereof, for the preparation of a catalyst of the present invention may be selected, e.g., from those described herein the illustrative examples. Further examples of such transition metal salts may be found, e.g., in Seyden-Penne, *Chiral Auxiliaries and Ligands in Asymmetric Synthesis*, John Wiley & Sons, Inc., NY (1995), which is hereby incorporated by reference. The catalyst may be generated in situ, or it can be isolated prior to use.

The chiral transition metal catalyst includes a suitable transition metal bound to a compound of the formula (I).

Suitable transition metals for the catalyst system include, but are not limited to copper (Cu), iridium (Ir), nickel (Ni), palladium (Pd), platinum (Pt), rhodium (Rh) and ruthenium (Ru) and salts thereof. Particularly useful, e.g., is copper and salts thereof.

Particularly useful in the present invention are catalysts wherein the transition metal is copper, and the transition metal is bound to a compound of formula [(I), wherein R is optionally substituted phenyl, R' is methyl, and R" is hydrogen; or an enantiomer thereof; or an enantiomeric mixture thereof. Examples of such catalysts include, but are not limited to, Cu(II) bound to (S)—P-Phos and Cu(II) bound to (S)-Xyl-P-Phos. The copper, e.g., may be present in the catalyst in a salt form. Salt forms of copper include, but are not limited to, $CuF_2$, $CuCl_2$, CuCl, $CuBr_2$, CuBr and CuI. These catalysts have also been found to be stable in air and in the presence of oxygen. Moreover, the catalysts of the present invention, e.g., are stable in the presence of oxidizing agents.

The above-mentioned catalyst systems, e.g., are particularly useful for the hydrosilylations of unfunctional ketones. Furthermore, the catalyst systems are provide a highly effective system for the hydrosilylation of a wide array of aryl alkyl ketones without the need for adding an organic or inorganic base. Such reactions can be conducted under air atmosphere and at mild temperatures. As used herein, the term "mild temperature" means a temperature ranging from room temperature (RT) to −20° C. Furthermore, the hydrosilylation source, that is hydride donor, can be, e.g., a silane, e.g., phenylsilane ($PhSiH_3$), PMHS, diphenylsilane ($Ph_2SiH_2$), ($PhMeSiH_2$) and ($Et_2SiH_2$).

Each of the hydrosilylation reactions (discussed below) is conducted in accordance with the following representative example which represents entry number 5 of Table 1, infra.

$CuF_2$ (5.4 mg, 0.054 mmol) and (S)-Xyl-P-Phos (1b, 2.1 mg, 2.72×10⁻³ mmol) are weigh under air and placed in a 25 mL round-bottomed flask equipped with a magnetic stirrer. Toluene (5.4 mL) is added and the mixture is stirred at RT for 10 minutes. Phenylsilane (800 μL, 6.43 mmol) and acetophenone (2a, 640 μL, 5.43 mmol) are sequentially added under vigorous stirring, and the flask is stoppered. The reaction is monitored by thin layer chromatography. Upon completion, the reaction mixture is treated with 10% HCl (3 mL), and the organic product is extracted with ether (3×20 mL). The combined extract is washed with water, dried with anhydrous sodium sulfate, filtered through a plug of silica and concentrated in vacuo to give the crude product. The conversion and the ee of the product (S)-1-phenylethanol[(S)-3a] are determined by NMR and chiral gas chromatography analysis to be >99% and 77%, respectively (column, Chirasil-DEX CB; 25 m×0.25 mm, CHROMPACK, carrier gas, $N_2$). The pure product is isolated by column chromatography (ethyl acetate:hexane=1:4).

For analysis, $^1H$ NMR, $^{13}C$ NMR and $^{31}P$ NMR spectra are recorded in $CDCl_3$ on a Varian AS 500 (500, 202 and 125 MHz, respectively) at RT. Chemical shifts (δ) are given in ppm and are referenced to residual solvent peaks ($^1H$ NMR, $^{13}C$ NMR) or to an external standard (85% $H_3PO_4$, $^{31}P$ NMR). Ee's of the asymmetric hydrosilylation products are determined by chiral GC and HPLC. Gas chromatographic analyses are conducted on an HP 4890A with an FID detector. HPLC analyses are performed using a Waters Model 600 with a Waters 486 UV detector. Optical rotations are measured on a Perkin-Elmer Model 341 polarimeter in a 10 cm cell. Optically pure P-Phos (1a), and Xyl-P-Phos (1b) are synthesized as stated in the following articles: Cheng-Chao Pai et al., *Highly effective chiral dipyridylphosphine ligands; synthesis, structural determination, and applications in the Ru-catalyzed asymmetric hydrogenation reactions*, 122 J. AM. CHEM. SOC. 11513-514 (2000) and Jing Wu et al., *A new chiral dipyridylphosphine ligand Xyl-P-Phos and its application in the Ru-catalyzed asymmetric hydrogenation of β-ketoesters*, 43 TETRAHEDRON LETT. 1539-43 (2002), which are both hereby incorporated by reference in their entirety. Copper fluoride, phenylsilane, PMHS and ketone substrates were purchased from Sigma-Aldrich Co. (St. Louis, Mo.) or Fisher-Scientific (Acros Organics) (Hampton, N.H.) and used as received without further purification unless otherwise stated.

A series of copper(I) and copper(II) halides are examined in the hydrosilylation of acetophenone (2a) in toluene at ambient temperature and under $N_2$ atmosphere employing (S)-1a ligand and $PhSiH_3$ as a hydride donor. Shown below in Scheme 1.

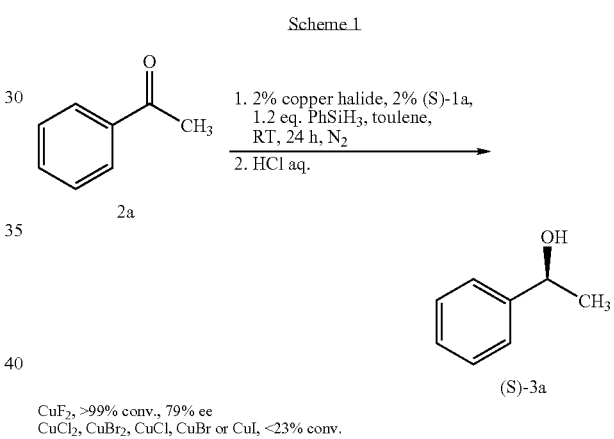

Scheme 1

$CuF_2$, >99% conv., 79% ee
$CuCl_2$, $CuBr_2$, CuCl, CuBr or CuI, <23% conv.

The reaction rate largely relies on the choice of halogen in copper salts and fluoride in the copper precursor is important for the generation of an active catalyst. $CuF_2$ provides a desirable product, i.e., (S)-3a in quantitative yield with 79% ee after 24 hours. In contrast, other Cu(I) and Cu(II) salts showed lesser reactivities (i.e., conversions less than 23%) under otherwise identical conditions.

As shown in Table 1, various catalyst systems with $CuF_2$ and varying ligands are examined in the hydrosilylation of acetophenone 2a. The reaction conditions are such that between 120-700 mg substrate are reduced at a substrate concentration of 0.6-1 M in toluene. The absolute configuration is determined by comparison with the retention times as found in the data of Takeshi Ohkuma et al., *Asymmetric hydrogenation of alkenyl, cyclopropyl, and aryl ketones. $RuCl_2$(xylbinap)(1,2-diamine) as a precatalyst exhibiting a wide scope*, 120 J. AM. CHEM. SOC. 13529-30 (1998) (hereinafter "Ohkuma").

TABLE 1

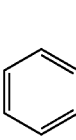

| Entry | CuF$_2$, mol % | Ligand | S/L | T, °C | Atm. | Time | Conv., % | ee,* % |
|---|---|---|---|---|---|---|---|---|
| 1 | 3 | (S)-1a | 33 | RT | N$_2$ | 3 h | 20 | 78 (S) |
| 2 | 1 | (S)-1a | 2000 | RT | Air | 25 min | 52 | 77 (S) |
| 3 | 1 | (S)-1a | 2000 | RT | Air | 3 h | >99 | 78 (S) |
| 4 | 3 | (S)-1b | 33 | RT | N$_2$ | 3 h | 63 | 76 (S) |
| 5 | 1 | (S)-1b | 2000 | RT | Air | 10 min | >99 | 77 (S) |
| 6 | 1 | (R)-BINAP | 2000 | RT | Air | 25 min | 14 | 73 (R) |
| 7† | 0.5 | (S)-BINAP | 200 | RT | Air | 6 h | 94 | 78 (S) |
| 8 | 3 | (S)-1a | 33 | −20 | Air | 24 h | 91 | 89 (S) |
| 9 | 3 | (S)-1b | 100 | −20 | Air | 6 h | >99 | 87 (S) |

Table 1 also shows that the presence of air in the reaction system markedly and surprisingly enhances the reaction rate. For example, when the hydrosilylation of 2a is carried out with 3 mol % CuF$_2$ and (S)-Xyl-P-Phos (1b) at RT under N$_2$, 63% conversion is observed after three hours. In contrast, under air, complete conversion is observed in only several minutes at a S/L of 2,000 with no diminution of enantioselectivity. Moreover, this is faster than that of the parent ligand P-Phos (1a). A direct comparison of the catalytic activities of P-Phos (1a) and Xyl-P-Phos (1b) compared with 2,2'-bis (diphenylphosphino)-1,1'-binaphtyl (BINAP) shows that the systems both with 1a and 1b are superior to that of the system with BINAP [the data for entry 7 is taken from Sabine Sirol, et al., *Efficient enantioselective hydrosilylation of ketones catalyzed by air stable copper fluoride-phosphine complexes*, 3 ORG. LETT. 4111-13 (2001). Further investigation shows that the lowering of the reaction temperature from room temperature to −20° C. enhances the enantioselectivity.

Table 2 shows the asymmetric hydrosilylation of aryl alkyl ketones 2 catalyzed by Cu(II) and dipyridylphosphine 1 under air atmosphere.

TABLE 2

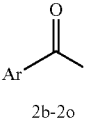

| Entry | Ketone | Ar | R$_a$ | CuF$_2$, mol % | Ligand | S/L | T, °C | Time | ee,* % |
|---|---|---|---|---|---|---|---|---|---|
| 1 | 2b | C$_6$H$_5$ | CH$_2$CH$_3$ | 3 | (S)-1b | 100 | −20 | 12 h | 93 |
| 2 | 2c | 2'-naphthyl | CH$_3$ | 3 | (S)-1b | 100 | −20 | 24 h | 92 |
| 3 | 2d | 2-CH$_3$C$_6$H$_4$ | CH$_3$ | 3 | (S)-1b | 100 | −20 | 24 h | 72 |
| 4 | 2e | 2-ClC$_6$H$_4$ | CH$_3$ | 3 | (S)-1b | 100 | −20 | 10 h | 77 |
| 5 | 2f | 2-BrC$_6$H$_4$ | CH$_3$ | 3 | (S)-1b | 100 | −20 | 10 h | 70 |
| 6 | 2g | 3-CH$_3$C$_6$H$_4$ | CH$_3$ | 3 | (S)-1b | 100 | −20 | 12 h | 87 |
| 7 | 2h | 3-CH$_3$OC$_6$H$_4$ | CH$_3$ | 3 | (S)-1b | 100 | −20 | 12 h | 92 |
| 8 | 2i | 3-BrC$_6$H$_4$ | CH$_3$ | 3 | (S)-1b | 100 | −20 | 12 h | 89 |
| 9 | 2j | 3-CF$_3$C$_6$H$_4$ | CH$_3$ | 3 | (S)-1b | 100 | −20 | 12 h | 91 |
| 10 | 2k | 4-CH$_3$C$_6$H$_4$ | CH$_3$ | 3 | (S)-1b | 100 | −20 | 24 h | 91 |
| 11 | 2l | 4-ClC$_6$H$_4$ | CH$_3$ | 3 | (S)-1b | 100 | −20 | 6 h | 94 |
| 12 | 2m | 4-BrC$_6$H$_4$ | CH$_3$ | 3 | (S)-1b | 100 | −20 | 6 h | 96 |
| 13 | 2n | 4-CF$_3$C$_6$H$_4$ | CH$_3$ | 3 | (S)-1a | 33 | −20 | 24 h | 96 |
| 14 | 2n | 4-CF$_3$C$_6$H$_4$ | CH$_3$ | 3 | (S)-1b | 100 | −20 | 6 h | 94 |
| 15 | 2o | 4-NO$_2$C$_6$H$_4$ | CH$_3$ | 1 | (S)-1b | 100 | RT | 1 h | 93 |
| 16 | 2o | 4-NO$_2$C$_6$H$_4$ | CH$_3$ | 3 | (S)-1b | 100 | −20 | 4 h | 97 |
| 17 | 2o | 4-NO$_2$C$_6$H$_4$ | CH$_3$ | 1.2 | (S)-1b | 20,000 | RT | 30 min | 91 |
| 18† | 2o | 4-NO$_2$C$_6$H$_4$ | CH$_3$ | 1.2 | (S)-1b | 100,000 | RT | 20 h | 90 |
| 19 | 2o | 4-NO$_2$C$_6$H$_4$ | CH$_3$ | 3 | (S)-1b | 50,000 | −10 | 48 h | 94 |
| 20 | 2m | 4-BrC$_6$H$_4$ | CH$_3$ | 3 | (S)-1b | 50,000 | −10 | 48 h | 93 |

Reaction conditions: 100 mg-42 g substrate, substrate concentration = 0.6-1 M toluene, >99% conversion is observed in all cases.
*The absolute configuration is determined by comparison of the sign of optical rotation or the retention times with the data of Ohkuma.
†The yield of the product isolated by column chromatography is 95%.

Complete hydrosilylations of most substrates by using 1b is realized in a few hours, e.g., 4-12 hours. The positioning of the substituents on the aromatic ring of acetophenone effects the outcome of the reaction. For example, the ortho-substituted acetophenones (2d-2f) are converted to the desired alcohols with moderate enantioselectivities (between 70-77% ee), while meta- and para-substituted acetophenones (2g-2o) gives consistently high enantioselectivities (87-97% ee).

To further evaluate the activity and air-stability of the present catalyst, the experiment of reducing 2o in air at RT with a S/L ratio 20,000 is conducted. No unreacted 2o is detected after only thirty minutes. Moreover, this reaction works even when the S/L ratio is increased to as high as 100,000. Thus, in the presence of only 2 mg of (S)-1b, hydrosilylation of 42 g 2o proceeds smoothly at RT under normal atmosphere and leads to 100% conversion within thirty hours to furnish (S)-3o bearing consistently high enantioselectivity. Furthermore, catalytic efficiency of (S)-1b/ $CuF_2$/$PhSiH_3$ is confirmed by carrying out the reactions at $-10°$ C. with S/L ratios of 50,000. Net conversions and high enantioselectivities are maintained for the hydrosilylation of both 2m and 2o. These results indicate that the activity of this air-accelerated copper (II)-catalyst system using dipyridylphosphine ligand is significantly greater than that employing BINAP.

It is known that a usual problem associated with the use of metal phosphine catalysts is their air-sensitivity, especially in solution, and trace amounts of air in the reaction system often destroy the active catalysts and make irreproducible results. Surprisingly in the reactions of the present invention, air enhances reaction rates.

The following lists the conditions of the analyses of the chiral secondary alcohols of Tables 1 and 2, i.e., 3a-5h.

1-Phenylethanol (3a). Capillary GC, Chirasil-DEX CB column; $120°$ C.; isothermal; $t_R$ (2a)=5.25 min; $t_R$(R)=10.36 min; $t_R$ (S)=11.09 min.

1-Phenylpropanol (3b). Capillary GC, Chirasil-DEX CB column; $122°$ C.; isothermal; $t_R$ (2b)=7.35 min; $t_R$(R)=15.62 min; $t_R$ (S)=16.12 min.

1-(2'-Naphthyl)ethanol (3c). Capillary GC, Chirasil-DEX CB column; $160°$ C.; isothermal; $t_R$ (2c)=13.40 min; $t_R$(R)=20.71 min; $t_R$ (S)=21.65 min.

1-(2-Methylphenyl)ethanol (3d). Capillary GC, Chirasil-DEX CB column; $140°$ C.; isothermal; $t_R$ (2d)=3.79 min; $t_R$(R)=7.78 min; $t_R$ (S)=8.90 min.

1-(2-Chlorophenyl)ethanol (3e). Capillary GC, Chirasil-DEX CB column; $145°$ C.; isothermal; $t_R$ (2e)=4.91 min; $t_R$(R)=9.40 min; $t_R$ (S)=11.02 min.

1-(2-Bromophenyl)ethanol (3f). Capillary GC, Chirasil-DEX CB column; $150°$ C.; isothermal; $t_R$ (2f)=5.21 min; $t_R$(R)=11.79 min; $t_R$ (S)=14.48 min.

1-(3-Methylphenyl)ethanol (3g). Capillary GC, Chirasil-DEX CB column; $122°$ C.; isothermal; $t_R$ (2g)=6.90 min; $t_R$(R)=14.02 min; $t_R$ (S)=15.05 min.

1-(3-Methoxyphenyl)ethanol (3h). Capillary GC, Chirasil-DEX CB column; $135°$ C.; isothermal; $t_R$ (2h)=8.11 min; $t_R$(R)=16.50 min; $t_R$ (S)=17.63 min.

1-(3-Bromophenyl)ethanol (3i). Capillary GC, Chirasil-DEX CB column; $145°$ C.; isothermal; $t_R$ (2i)=6.65 min; $t_R$(R)=15.19 min; $t_R$ (S)=16.32 min.

1-(3-Trifluoromethylphenyl)ethanol (3j). Capillary GC, Chirasil-DEX CB column; $125°$ C.; isothermal; $t_R$ (2i)=3.82 min; $t_R$(R)=9.90 min; $t_R$ (S)=11.06 min.

1-(4-Methylphenyl)ethanol (3k). Capillary GC, Chirasil-DEX CB column; $125°$ C.; isothermal; $t_R$ (2k)=6.93 min; $t_R$(R)=10.78 min; $t_R$ (S)=12.01 min.

1-(4-Chlorophenyl)ethanol (3l). Capillary GC, Chirasil-DEX CB column; $144°$ C.; isothermal; $t_R$ (2l)=5.75 min; $t_R$(R)=10.89 min; $t_R$ (S)=11.97 min.

1-(4-Bromophenyl)ethanol (3m). Capillary GC, Chirasil-DEX CB column; $150°$ C.; isothermal; $t_R$ (2m)=6.87 min; $t_R$(R)=13.02 min; $t_R$ (S)=14.15 min.

1-(4-Trifluoromethylphenyl)ethanol (3n). Capillary GC, Chirasil-DEX CB column; $125°$ C.; isothermal; $t_R$ (2n)=4.72 min; $t_R$(R)=12.38 min; $t_R$ (S)=14.53 min.

1-(4-Nitrophenyl)ethanol (3o). Capillary GC, Chirasil-DEX CB column; $172°$ C.; isothermal; $t_R$ (2o)=5.86 min; $t_R$(R)=14.01 min; $t_R$ (S)=15.30 min.

o-Chlorobenzhydrol (5a). The conversion is determined by capillary GC with a 30 m×0.25 mm J & W Scientific INNOWAX column; $232°$ C.; isothermal; $t_R$ (4a)=8.60 min; $t_R$ (5a)=14.88 min. The ee value is determined by chiral HPLC analysis with a 25 cm×4.6 mm Daicel Chiralcel OD column (eluent, 10:90 2-propanal-hexane; flow rate=1.0 mL/min; detection: 254 nm light); $t_R$ (R)=8.33 min; $t_R$ (S)=10.33 min.

o-Fluorobenzhydrol (5b). The conversion is determined by capillary GC with a 30 m×0.25 mm J & W Scientific INNOWAX column; $230°$ C.; isothermal; $t_R$ (4b)=6.23 min; $t_R$ (5b)=9.95 min. The ee value is determined by chiral HPLC analysis with a 25 cm×4.6 mm Daicel Chiralcel OD column (eluent, 4:96 2-propanal-hexane; flow rate=0.4 mL/min; detection: 254 nm light); $t_R$ (R)=29.96 min; $t_R$ (S)=34.35 min.

o-Methylbenzhydrol (5c). The conversion is determined by capillary GC with a 30 m×0.25 mm J & W Scientific INNOWAX column; $230°$ C.; isothermal; $t_R$ (4c)=6.18 min; $t_R$ (5c)=11.76 min. The ee value is determined by chiral HPLC analysis with a 25 cm×4.6 mm Daicel Chiralcel OB-H column (eluent, 10:90 2-propanal-hexane; flow rate=0.5 mL/min; detection: 254 nm light); $t_R$ (R)=19.96 min; $t_R$ (S)=21.74 min.

o-Trifluoromethylbenzhydrol (5d). The conversion is determined by capillary GC with a 30 m×0.25 mm J & W Scientific INNOWAX column; $230°$ C.; isothermal; $t_R$ (4d)=5.06 min; $t_R$ (5d)=6.96 min. The ee value is determined by chiral HPLC analysis with a 25 cm×4.6 mm Daicel Chiralcel OD column (eluent, 10:90 2-propanal-hexane; flow rate=0.9 mL/min; detection: 254 nm light); $t_R$ (R)=6.39 min; $t_R$ (S)=7.64 min.

m-Methylbenzhydrol (5e). The conversion is determined by capillary GC with a 30 m×0.25 mm J & W Scientific INNOWAX column; $232°$ C.; isothermal; $t_R$ (4e)=6.90 min; $t_R$ (5e)=10.73 min. The ee value is determined by chiral HPLC analysis with a 25 cm×4.6 mm Daicel Chiralcel OB-H column (eluent, 10:90 2-propanal-hexane; flow rate=0.9 mL/min; detection: 254 nm light); $t_R$=14.96 min (minor) and 27.55 min (major).

p-Chlorobenzhydrol (5f). The conversion is determined by capillary GC with a 30 m×0.25 mm J & W Scientific INNOWAX column; $232°$ C.; isothermal; $t_R$ (4f)=9.20 min; $t_R$ (5f)=19.93 min. The ee value is determined by chiral HPLC analysis with a 25 cm×4.6 mm Daicel Chiralcel OB-H column (eluent, 10:90 2-propanal-hexane; flow rate=0.8 mL/min; detection: 254 nm light); $t_R$ (R)=19.98 min; $t_R$ (S)=29.03 min.

p-Methylbenzhydrol (5g). The conversion is determined by capillary GC with a 30 m×0.25 mm J & W Scientific INNOWAX column; $230°$ C.; isothermal; $t_R$ (4g)=8.13 min; $t_R$ (5g)=12.28 min. The ee value is determined by chiral HPLC analysis with a 25 cm×4.6 mm Daicel Chiralcel OB-H column (eluent, 10:90 2-propanal-hexane; flow rate 0.4 mL/min; detection: 254 nm light). $t_R$ (R)=28.90 min; $t_R$ (S)=33.38 min.

p-Trifluoromethylbenzhydrol (5h). The conversion is determined by capillary GC with a 30 m×0.25 mm J & W Scientific INNOWAX column; 230° C.; isothermal; $t_R$ (4h)=4.67 min; $t_R$ (5h)=9.62 min. The ee value is determined by chiral HPLC analysis with a 25 cm×4.6 mm Daicel Chiralcel OB-H column (eluent, 10:90 2-propanal-hexane; flow rate=0.8 mL/min; detection: 254 nm light); $t_R$ (R)=9.17 min; $t_R$ (S)=11.95 min.

Table 3 shows the asymmetric hydrosilylation of substituted benzophenones 4 catalyzed by Cu(II) and dipyridylphosphine 1 under air atmosphere.

TABLE 3

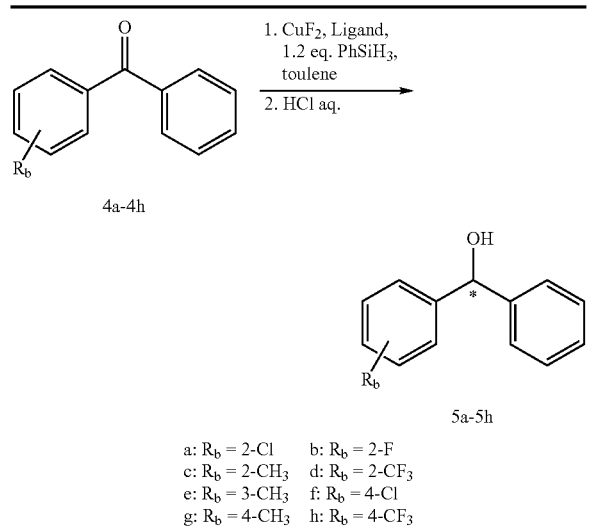

a: $R_b$ = 2-Cl    b: $R_b$ = 2-F
c: $R_b$ = 2-CH$_3$  d: $R_b$ = 2-CF$_3$
e: $R_b$ = 3-CH$_3$  f: $R_b$ = 4-Cl
g: $R_b$ = 4-CH$_3$  h: $R_b$ = 4-CF$_3$

| Entry | Ketone | CuF$_2$, mol % | Ligand [mol %] | T, °C. | Time, h | Conv, % | ee,* % |
|---|---|---|---|---|---|---|---|
| 1 | 4a | 3 | (S)-1a [3] | RT | 30 | 96 | 81 (R) |
| 2 | 4a | 4 | (S)-1a [4] | −10 | 72 | 99 | 90 (R) |
| 3 | 4a | 4 | (S)-1b [4] | −10 | 48 | 82 | 91 (R) |
| 4 | 4b | 4 | (S)-1a [4] | −10 | 48 | >99 | 63 (R) |
| 5 | 4b | 4 | (S)-1b [4] | −10 | 48 | >99 | 75 (R) |
| 6 | 4c | 4 | (S)-1a [4] | −10 | 72 | 99 | 83 (R) |
| 7 | 4c | 4 | (S)-1b [4] | −10 | 48 | >99 | 75 (R) |
| 8 | 4d | 4 | (S)-1a [4] | −10 | 72 | 85 | 98 (R)† |
| 9 | 4d | 4 | (5)-1b [4] | −10 | 48 | 88 | 95 (R)† |
| 10 | 4e | 4 | (S)-1b [4] | −10 | 48 | >99 | 6 (+) |
| 11 | 4f | 4 | (S)-1a [4] | −10 | 48 | >99 | 36 (S) |
| 12 | 4f | 4 | (S)-1b [4] | −10 | 48 | >99 | 43 (S) |
| 13 | 4g | 4 | (S)-1a [4] | −10 | 48 | >99 | 27 (S) |
| 14 | 4g | 4 | (S)-1b [4] | −10 | 48 | >99 | 39 (S) |
| 15 | 4h | 4 | (S)-1a [4] | −10 | 48 | >99 | 25 (S) |
| 16 | 4h | 4 | (S)-1b [4] | −10 | 48 | >99 | 41 (S) |

Reaction conditions: 100-150 mg substrate, substrate concentration = 0.6-1 M in toluene.
*The absolute configuration was determined by comparison of the sign of optical rotation or the retention times with the data of the following reference: Takeshi Ohkuma et al., Selective hydrogenation of benzophenones to benzhydrols. Asymmetric synthesis of unsymmetrical diaryl methanols, 2 ORGANIC LETT. 659-62 (2000).
†The absolute configuration of 5d was determined by comparison of the sign of optical rotation with the data of refs. Eric Brown et al., Determination of the ee's of chiral acids by $^{19}$F NMR studies of their esters deriving from (R)-(+)-2-(trifluoromethyl)benzhydrol, 5 TETRAHEDRON: ASYMMETRY 1191-94 (1994) and Junpai Naito et al, Enantioresolution of fluorinated diphenylmethanols and determination of their absolute configurations by X-Ray crystallographic and $^1$HNMR anisotropy methods, 16 CHIRALITY 22-35 (2004).

Similar to aryl alkyl ketones, a lower reaction temperature give higher enantioselectivity at the expense of reaction rate. A range of ortho-substituted benzophenones (4a-4-d) are reduced to benzhydrols with good to excellent enantioselectivity. In the case of 4d, the highest enantioselectivity of 98% ee is attained at −100° C. with (S)-1a ligand. In addition, substrates with a bulkier ortho-substituent reacted favorably to give products of higher enantiopurities. Without being bound to any particular theory, it appears that steric effects of the ortho substituents affect the extent of the coplanarity of the benzene rings with C=O function in the transition state, thereby generating an asymmetric bias. Meta- and para-substituted benzophenones (4e-4h) are transformed to the corresponding alcohols with low to moderate enantioselectivities. Notably, (S)-1a or (S)-1b afforded ortho-substituted benzhydrols with (R)-configurations, while the absolute configurations are inversed for para-substituted products.

Thus, the present invention provides a method for the hydrosilylation of asymmetrical diaryl ketones to benzhydrol with excellent ee values, i.e., especially ortho-substituted benzophenones with ee's up to 98%.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed is:

1. A method for converting a prochiral substrate that is a prochiral ketone to a chiral product that is an alcohol by asymmetric hydrosilylation in the presence of a catalyst comprising a transition metal bound to a compound of the formula (I):

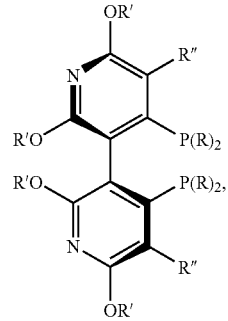

Compound (1)

wherein
R is optionally substituted alkyl, cycloalkyl, aryl or heteroaryl;
R' is alkyl or aryl; and
R" is hydrogen, halogen, optionally substituted alkyl, hydroxyl, amino, or alkenyl;
or an enantiomer thereof; or an enantiomeric mixture thereof.

2. The method of claim 1,
wherein
R is phenyl;
R' is methyl; and
R" is hydrogen;
or an enantiomer thereof; or an enantiomeric mixture thereof.

3. The method of claim 1,
wherein
R is a substituted phenyl;
R' is methyl; and
R" is hydrogen;
or an enantiomer thereof; or an enantiomeric mixture thereof.

4. The method of claim 3, wherein R is 3,5-(CH$_3$)$_2$C$_6$H$_3$; or an enantiomer thereof; or an enantiomeric mixture thereof.

5. The method of claim 1, wherein the transition metal is selected from the group consisting of copper, iridium, nickel, palladium, platinum, rhodium and ruthenium and salts thereof.

6. The method of claim 5, wherein the transition metal is copper.

7. The method of claim 1, wherein the prochiral ketone is a benzophenone and the alcohol is a benzhydrol.

8. A method for converting a prochiral substrate that is a prochiral ketone to a chiral product that is an alcohol by asymmetric hydrosilylation in the presence of a catalyst and without the addition of a base comprising a transition metal bound to a compound of the formula (I):

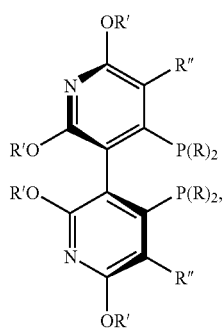

Compound (1)

wherein
R is optionally substituted alkyl, cycloalkyl, aryl or heteroaryl;
R' is alkyl or aryl; and
R" is hydrogen, halogen, optionally substituted alkyl, hydroxyl, amino, or alkenyl;
or an enantiomer thereof; or an enantiomeric mixture thereof.

9. The method of claim 8,
wherein
R is phenyl;
R' is methyl; and
R" is hydrogen;
or an enantiomer thereof; or an enantiomeric mixture thereof.

10. The method of claim 8,
wherein
R is a substituted phenyl;
R' is methyl; and
R" is hydrogen;
or an enantiomer thereof; or an enantiomeric mixture thereof.

11. The method of claim 10, wherein R is 3,5-$(CH_3)_2C_6H_3$; or an enantiomer thereof; or an enantiomeric mixture thereof.

12. The method of claim 8, wherein the transition metal is selected from the group consisting of copper, iridium, nickel, palladium, platinum, rhodium and ruthenium and salts thereof.

13. The method of claim 12, wherein the transition metal is copper.

14. The method of claim 8, wherein the prochiral ketone is a benzophenone and the alcohol is a benzhydrol.

15. The method of claim 8, wherein the method is conducted at mild temperature.

16. The method of claim 8, wherein the method is conducted in the presence of air.

17. The method of claim 8, wherein the method uses a high S/L ratio.

18. The method of claim 8, wherein the SIL ratio is from 20,000-500,000.

19. The method of claim 17, wherein said reaction includes a silane as a hydride donor.

* * * * *